(12) United States Patent
Lee et al.

(10) Patent No.: US 8,853,279 B2
(45) Date of Patent: Oct. 7, 2014

(54) METHOD FOR DETERMINING SENSITIVITY OR RESISTANCE TO COMPOUNDS THAT ACTIVATE THE BRAIN SEROTONIN SYSTEM

(75) Inventors: Francis S. Lee, New York, NY (US); Barbara Hempstead, New York, NY (US); James Kocsis, Roxbury, CT (US); Kevin Bath, Rumford, RI (US)

(73) Assignee: Cornell University, Ithaca, NY (US)

( * ) Notice: Subject to any disclaimer, the term of this patent is extended or adjusted under 35 U.S.C. 154(b) by 288 days.

(21) Appl. No.: 12/999,581

(22) PCT Filed: Jun. 16, 2009

(86) PCT No.: PCT/US2009/047567
§ 371 (c)(1),
(2), (4) Date: May 9, 2011

(87) PCT Pub. No.: WO2010/071694
PCT Pub. Date: Jun. 24, 2010

(65) Prior Publication Data
US 2011/0207827 A1 Aug. 25, 2011

Related U.S. Application Data

(60) Provisional application No. 61/061,836, filed on Jun. 16, 2008.

(51) Int. Cl.
*A61K 31/135* (2006.01)
*C12Q 1/68* (2006.01)

(52) U.S. Cl.
CPC ........ *C12Q 1/6883* (2013.01); *C12Q 2600/156* (2013.01); *C12Q 2600/106* (2013.01)
USPC .......... 514/651; 514/646; 514/649; 435/6.11; 435/6.13

(58) Field of Classification Search
USPC .......................................... 514/646, 649, 651
See application file for complete search history.

(56) References Cited

U.S. PATENT DOCUMENTS

2010/0240763 A1* 9/2010 Lee et al. .................. 514/651
2010/0304391 A1* 12/2010 Lombard ....................... 435/6

FOREIGN PATENT DOCUMENTS

WO WO2007084734 A2 7/2007

OTHER PUBLICATIONS

Nash et al., "Antidepressants", Jul. 2007, Psychiatry, vol. 6, Issue 7, pp. 289-294.*
Tsai et al., "Association Study of a Brain-Derived Neurotrophic-Factor Genetic Polymorphism and Major Depressive Disorders, Symptomatology, and Antidepressant Response", Nov. 15, 2003, American Journal of Medical Genetics Part B (Neuropsychiatric Genetics), vol. 123B, Issue 1, pp. 19-22.*
Pezawas et al., "The Brain-Derived Neurotrophic Factor val66met Polymorphism and Variation in Human Cortical Morphology," Journal of Neuroscience 2004, 24(45):10099-10102.
Egan et al., "The BDNF val66met Polymorphism Affects Activity-Dependent Secretion of BDNF and Human Memory and Hippocampal Function," Cell 2003, 112:257-269.
Saarelainen et al., "Activation of the TrkB Neurotrophin Receptor Is Induced by Antidepressant Drugs and Is Required for Antidepressant-Induced Behavioral Effects," Journal of Neuroscience 2003, 23(1):349-35T.

* cited by examiner

*Primary Examiner* — My-Chau T Tran
(74) *Attorney, Agent, or Firm* — Hoffmann & Baron, LLP

(57) ABSTRACT

The invention relates to a method for determining whether a patient suffering from a condition that is susceptible to treatment with a compound that activates the brain serotonin system is susceptible or resistant to treatment with the compound. The method includes establishing whether the patient is a pre-adult, a transition age patient, or an adult and observing whether the genome of the patient contains at least one copy of a BDNF allele having a genetic alteration. The method further includes correlating the presence of the allele containing the genetic alteration with susceptibility or resistance of the patient to the treatment with the compound, wherein a pre-adult patient containing the genetic alteration is correlated as being susceptible to the treatment; a transition age patient containing the genetic alteration is correlated as being susceptible or resistant to the treatment; and an adult patient containing the genetic alteration is correlated as being resistant to the treatment.

19 Claims, 11 Drawing Sheets

FIGURE 1

```
1   atgaccatcc ttttccttac tatggttatt tcatactttg gttgcatgaa ggctgccccc
61  atgaaagaag caaacatccg aggacaaggt ggcttggcct acccaggtgt gcggacccat
121 gggactctgg agagcgtgaa tgggcccaag gcaggttcaa gaggcttgac atcattggct
181 gacactttcg aacacgtgat agaagagctg ttggatgagg accagaaagt tcggcccaat
241 gaagaaaaca ataaggacgc agacttgtac acgtccaggg tgatgctcag tagtcaagtg
301 cctttggagc ctcctcttct ctttctgctg gaggaataca aaaattacct agatgctgca
361 aacatgtcca tgagggtccg gcgccactct gaccctgccc gccgagggga gctgagcgtg
421 tgtgacagta ttagtgagtg ggtaacggcg gcagacaaaa agactgcagt ggacatgtcg
481 ggcgggacgg tcacagtcct tgaaaaggtc cctgtatcaa aaggccaact gaagcaatac
541 ttctacgaga ccaagtgcaa tcccatgggt tacacaaaag aaggctgcag gggcatagac
601 aaaaggcatt ggaactccca gtgccgaact acccagtcgt acgtgcgggc ccttaccatg
661 gatagcaaaa agagaattgg ctggcgattc ataaggatag acacttcttg tgtatgtaca
721 ttgaccatta aaggggaag atag (SEQ ID NO: 1)
```

FIGURE 2

```
  1 mtilfltmvi syfgcmkaap mkeanirgqg glaypgvrth gtlesvngpk agsrgltsla
 61 dtfehvieel ldedqkvrpn eennkdadly tsrvmlssqv pleppllfll eeyknyldaa
121 nmsmrvrrhs dparrgelsv cdsisewvta adkktavdms ggtvtvlekv pvskgqlkqy
181 fyetkcnpmg ytkegcrgid krhwnsqcrt tqsyvraltm dskkrigwrf iridtscvct
241 ltikrgr (SEQ ID NO: 2)
```

METHOD FOR DETERMINING SENSITIVITY OR RESISTANCE TO COMPOUNDS THAT ACTIVATE THE BRAIN SEROTONIN SYSTEM

This application is a National Phase application of International Application No. PCT/U.S.2009/047567, filed Jun. 16, 2009, which claims priority to U.S. Provisional Patent Application No. 61/061,836, filed on Jun. 16, 2008, both of which are incorporated herein by reference in their entireties.

This invention described in this application was made with funds from the National Institutes of Health, grant number R01 NS052819. The U.S. government has rights in the invention.

BACKGROUND OF THE INVENTION

Brain-derived neurotrophic growth factor (BDNF) is a protein that is widely expressed in the human brain. The protein plays a critical role in the development and maintenance of neurons in the central nervous system and the peripheral nervous system. For example, BDNF helps to support the survival of existing neurons, and encourage the growth and differentiation of new neurons and synapses. In addition, BDNF has established roles in neuronal survival, differentiation, and synaptic plasticity.

In the brain, BDNF is active in the hippocampus, cortex, and basal forebrain. These areas are vital to learning, memory, and higher thinking. Previous reports have indicated a possible link between low levels of BDNF and psychiatric conditions such as mood disorders and depression.

Anti-depressants, such as selective serotonin reuptake inhibitors (SSRIs), are typically prescribed to patients suffering from psychiatric conditions, such as depression and anxiety disorders. However, some patients are resistant to SSRIs. The time period required to determine whether a patient will respond positively or be resistant to SSRI treatment can be costly and lengthy.

Currently, there is a method for determining whether a patient is resistant to such types of treatment. The method is described in patent application PCT/U.S.2007/001560. However, there are currently no methods to predict who will not only be resistant to the treatment, but also who will be responsive.

Therefore, there is a need for new methods for determining whether a patient suffering from a condition that may be susceptible to treatment with a compound that activates the brain serotonin system is actually susceptible or resistant to treatment with the compound.

SUMMARY OF THE INVENTION

In one aspect, the invention relates to a method for determining whether a patient suffering from a condition that may be susceptible to treatment with a compound that activates the brain serotonin system is susceptible or resistant to treatment with the compound. For instance, the invention relates to a method for determining whether a patient is susceptible or resistant to treatment with a compound that activates the brain serotonin system. The method includes establishing whether the patient is a pre-adult, a transition age patient, or an adult; observing whether the genome of the patient contains at least one copy of a BDNF allele having a genetic alteration; and correlating the presence of the allele containing the genetic alteration with susceptibility or resistance of the patient to the treatment with the compound, wherein a pre-adult patient containing the genetic alteration is correlated as being susceptible to the treatment; a transition age patient containing the genetic alteration is correlated as being susceptible or resistant to the treatment; and an adult patient containing the genetic alteration is correlated as being resistant to the treatment.

In another aspect, the invention relates to a method for promoting normal brain development in a pre-adult patient or a transition age patient whose genome contains at least one copy of a BDNF allele having a genetic alteration. The method includes prescribing an effective amount of a compound that upregulates BDNF levels until the patient is an adult.

BRIEF DESCRIPTION OF THE FIGURES

FIG. 1. Nucleotide sequence of wild type BDNF gene.

FIG. 2. GenBank Accession No. NP 001700. Amino acid sequence of wild type BDNF.

FIG. 4A shows the percentage of time spent in the open arm and the percentage of open arm entries of mice in the elevated plus maze. FIG. 4B shows the percentage of time spent in the center and percentage of entries to the center in the open field test. (C) In the novelty induced hypophagia (NIH) test, latency to begin drinking in a novel cage is shown in seconds. All results are presented as a mean±SEM determined from analysis of 8 mice/genotype (*$p<0.01$, Student t test).

Figure 3:
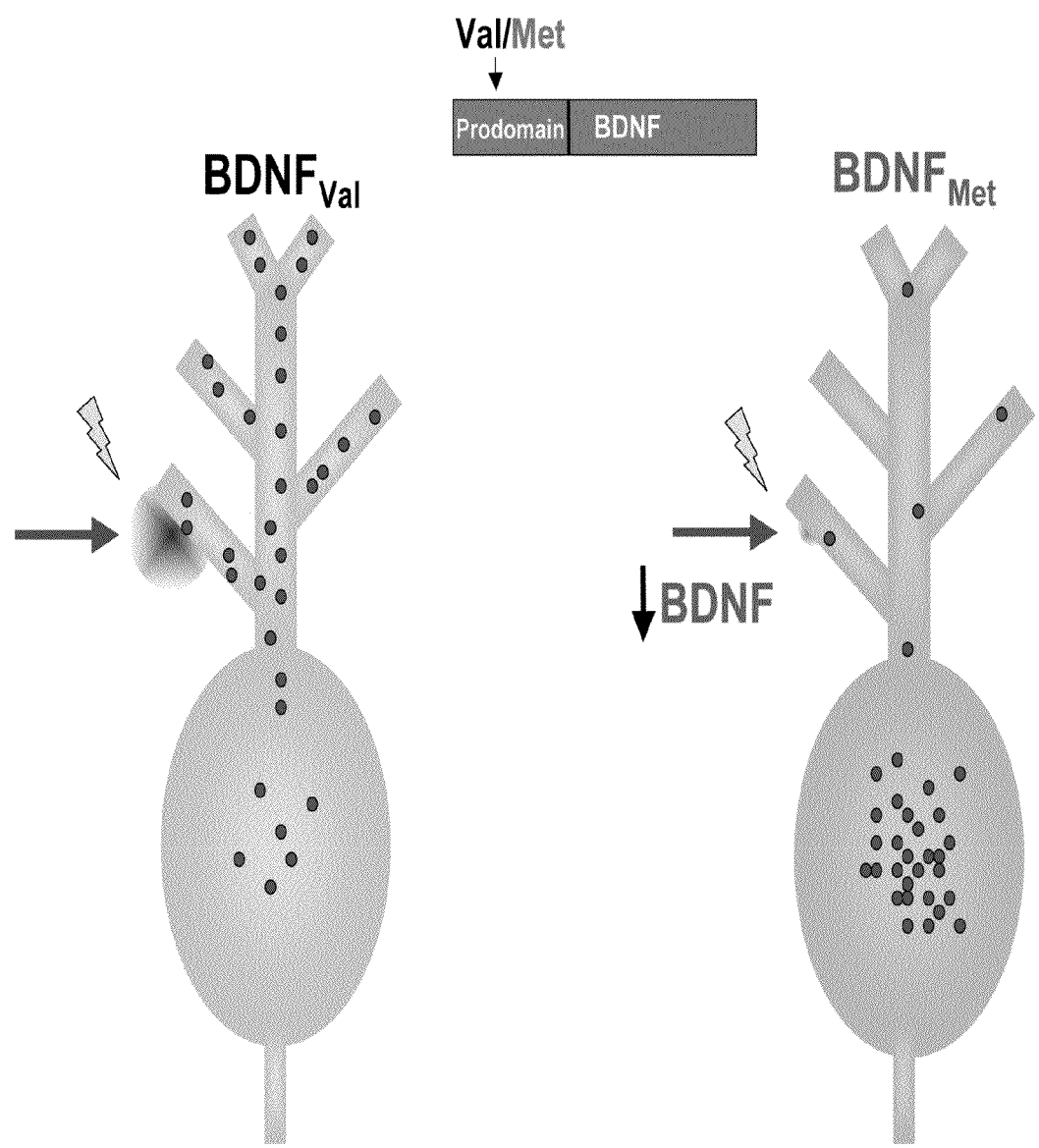
FIG. 3. Levels of BDNF and $BDNF_{Met}$ during development. (A) The schematic of FIG. 3A illustrates BDNF secretion from neurons. The neuron labeled $BDNF_{Val}$ represents a neuron in patients that are wild-type for the BDNF allele. The schematic of a neuron labeled $BDNF_{Met}$ represents a neuron in patients who have a Val66Met single nucleotide polymorhism (SNP). The genetic variant $BDNF_{Met}$ leads to decreased activity-dependent secretion of BDNF from neurons, resulting in decreased availability of biologically active BDNF. (B) BDNF levels during a "critical time" of postnatal development will have functional consequences on increased anxiety in adulthood (P60). Secretion of BDNF is decreased throughout this period of postnatal development (i.e., after P30 to P60) in mammals with a genetic variant $BDNF_{Met}$. The decreased BDNF secretion during this period of postnatal development is correlated with functional deficits after P30. Timed pharmacological administration of a compound that activates the brain serotonin system during this period will raise BDNF levels and rescue the anxiety endophenotype.
Figure 3:
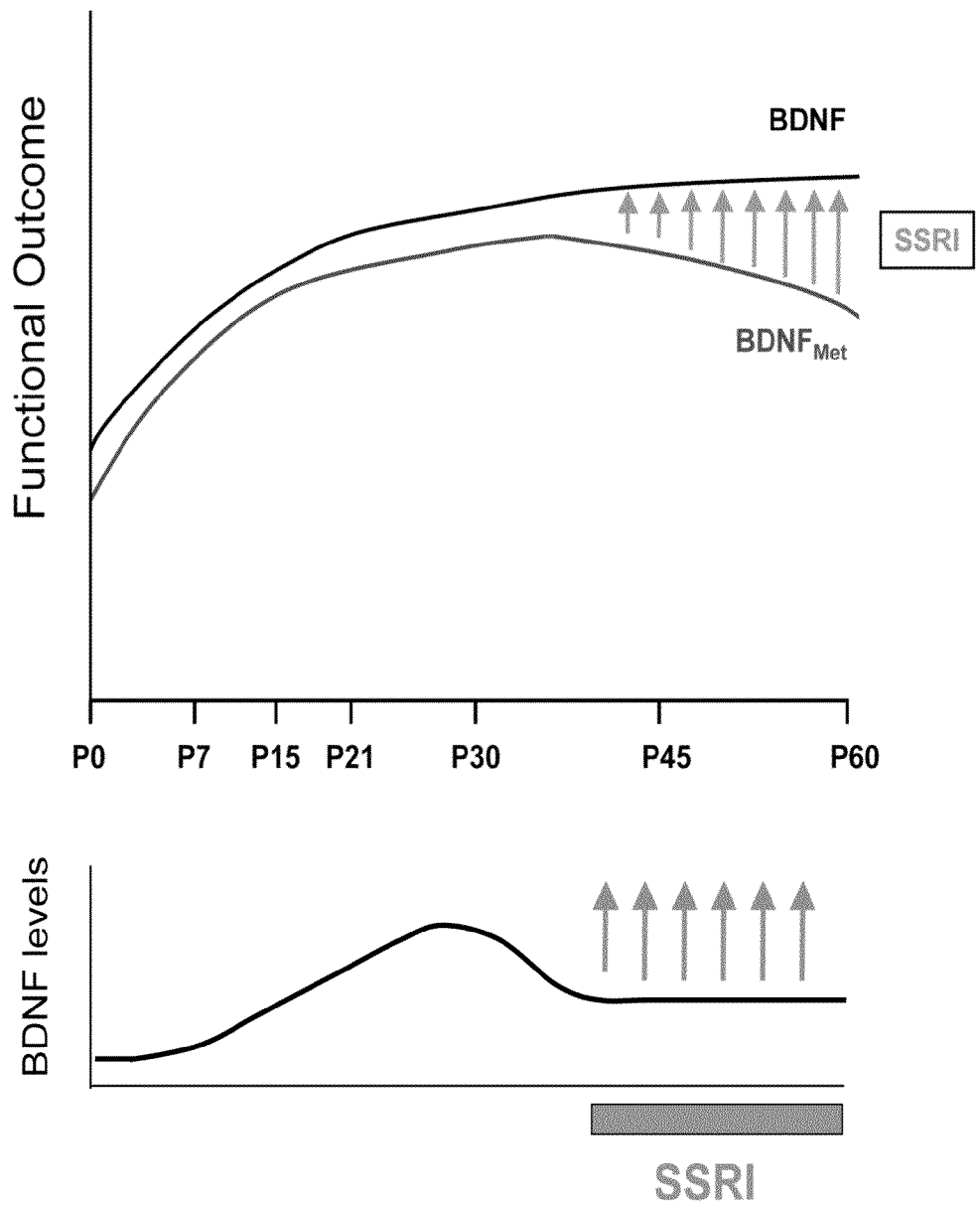

Percentage time spent in the open arm (B) and percentage of open arm entries in the plus maze, as well as (C) total distance traveled in wildtype) WT and BDNF$^{Met/Met}$ (Met/Met) mice treated with water ($H_2O$) or with flouxetine (FLX) from P21-P40. All results are presented as a mean±SEM determined from analysis of 5 mice/genotype (*p<0.05), Student's t test.

DETAILED DESCRIPTION OF THE INVENTION

This invention relates to a method for determining whether a patient suffering from a condition that may be susceptible to treatment with a compound that activates the brain serotonin system is actually susceptible or resistant to treatment with the compound.

The inventors surprisingly discovered that even small levels of brain-derived neurotrophic growth factor (BDNF) upregulation in mammals prior to the completion of their development can have a significant impact on normalizing development of the mammals. More specifically, the inventors discovered that when pre-adult mammals with an alteration in the BDNF allele are stimulated to upregulate BDNF, the brains of the pre-adults developed similarly to those of wild-type pre-adults upon reaching adulthood. The pre-adults with an alteration in the BDNF allele, who were treated, also demonstrated less anxiety in adulthood than did untreated mammals.

Establishing Whether the Patient is a Pre-Adult or an Adult

Surprisingly, therefore, whether a patient suffering from a condition that may be susceptible to treatment with a compound that activates the brain serotonin system is susceptible or resistant to treatment with the compound depends primarily on the age of the patient. Accordingly, a step in the method of the present invention is establishing whether the patient is a pre-adult, a transition age patient, or is an adult.

The term "pre-adult" refers to a patient that has not yet reached full growth and development. In a typical pre-adult patient, BDNF expression in the hippocampus of the patient is increasing or has leveled off.

A pre-adult patient is typically any age from one day old to approximately eighteen years old. The pre-adult patient can, for example, be a neonate, an infant, a pre-pubertal, a child, an early pubertal, a mid-pubertal, late pubertal, a pubescent, an adolescent, or a young adult.

The term "adult" refers to a patient that has reached full growth and development. In a typical adult patient, BDNF expression is decreasing in the hippocampus of the patient.

An adult patient is typically any age approximately 23 years or older. The adult patient can, for example, be post-pubertal, middle-aged, or elderly.

The line between the age at which patients are susceptible to treatment with a compound that activates the brain serotonin system and the age at which patients are not susceptible to such treatment is not sharp. Therefore, there is a transition age during which the patient may be susceptible or resistant to such treatment. The term transition age patient refers to a patient who is older than approximately 18 years old but younger than approximately 23 years old.

Because of patient to patient variability, the age ranges stated above are approximate. As used herein, the term "approximately" with respect to the age of a patient refers to the age being within plus or minus one year of the stated age.

The methods of the invention can be carried out by persons qualified to carry out the steps. Typically, the invention will be carried out by a medical practitioner, e.g., a physician, a psychologist, a clinician, a nurse, etc., or anyone else qualified to make the assessment.

Medical practitioners, e.g., physicians, who have the responsibility of deciding whether or not to prescribe and/or administer a compound that activates the brain serotonin system to a patient should, within the above guidelines, use their judgment in deciding whether such a compound is appropriate for a particular patient. The medical practitioner may consider factors other than actual age to establish the appropriateness of a particular treatment.

For example, if a patient is within the transition age group, or is close to the upper limit of the pre-adult age group, or the lower limit of the adult age group, or is within the variation of a range of approximate ages, a medical practitioner might consider the state of development of a patient. If the patient appears to be more developed than average for the age of the patient, a medical practitioner might be inclined to not prescribe treatment with a compound that activates the brain serotonin system. If the patient appears to be less developed than average for the age of the patient, a medical practitioner might be inclined to prescribe treatment with such a compound.

Another factor a medical practitioner might consider is the severity of the condition being treated. For example, if the condition poses a particularly serious threat to the patient, a medical practitioner will tend to be more aggressive in prescribing a treatment. If the condition poses a less serious threat to the patient, a medical practitioner will tend to be less aggressive in prescribing a treatment.

An additional factor for a medical practitioner's consideration is the susceptibility of a patient to known side effects of a treatment. If the patient is known to be susceptible to such side effects, a medical practitioner will tend to be cautious.

Accordingly, medical practitioners will be able to use their judgment in determining whether a patient should be considered to be a pre-adult, a transition age patient, or an adult. Prescribing medical practitioners will are trained to make such judgments.

Any method can be employed to establish whether the patient is a pre-adult or an adult. For example, establishing whether the patient is a pre-adult or an adult can be visually apparent or it can be provided by the patient or by a person familiar with the patient after an inquiry.

Observing Whether a Genome Contains a BDNF Allele Having an Alteration

Another step in the method of the present invention is observing whether the genome of the patient contains at least one copy of the brain-derived neurotrophic factor (BDNF) allele having a genetic alteration. The determination whether or not there is a genetic alteration may be carried out by the medical practitioner who is examining the patient, or by a third party. For example, the determination can be carried out by a laboratory technician in a laboratory that specializes in identifying genetic alterations. The laboratory then informs the medical practitioner of the results by, for example, providing the medical practitioner with a written or oral report. In such a case, the medical practitioner observes whether the genome of the patient contains at least one copy of the brain-derived neurotrophic factor (BDNF) allele having a genetic alteration by reading the report.

Brain-derived neurotrophic factor (BDNF) is a member of the neurotrophin family of proteins, a group of highly conserved polypeptide growth factors that also includes nerve growth factor, neurotrophin-3 (NT-3) and neurotrophin-4/5 (NT-4/5). BDNF binds to the TrkB receptor.

The BDNF gene, which in humans is found on chromosome 11, spans over 40 kB. Typically, the BDNF gene has at least four 5'-exons (exons I, II, III, and IV) that are associated with distinct promoters, and one 3'-exon (exon V). The wildtype BDNF gene comprises a nucleotide coding sequence of pre-pro-BDNF DNA, which is shown in FIG. 1. The nucleotide sequence that encodes the pre-domain, which is also referred to as the signal peptide, comprises the nucleotide sequence beginning at base 1 and ending at base 54 of FIG. 1. The nucleotide sequence that encodes the pro-domain comprises the sequence beginning at base 55 and ending at base 384 of FIG. 1. The nucleotide sequence that encodes the mature domain of the BDNF protein comprises the nucleotide sequence from base 385 to base 741 of FIG. 1.

The genome of a patient generally contains two BDNF alleles. An allele, as used herein, is any of one or more alternative forms of a gene. In an organism, two alleles of a given gene occupy corresponding loci on a pair of homologous chromosomes. For example, two alleles of a BDNF gene occupy corresponding loci on chromosome 11.

The term "genetic alteration," as used herein, refers to any changes in one or more of the nucleic acid molecules in the nucleotide coding sequence of wild-type BDNF that leads to a change in the amino acid sequence of wild-type BDNF. Accordingly, a BDNF allele that has a nucleotide coding sequence that leads to a change in the amino acid sequence different from the wild-type BDNF constitutes one or more genetic alterations. Examples of genetic alterations include one or more nucleotide additions, deletions, substitutions, etc, and combinations thereof. The genetic variation may, or may not, result in a frame shift.

Wild-type BDNF contains a pre-domain, a pro-domain and a mature domain. The genetic alteration may be in any one of these domains, in two of the domains such as in both the pro-domain and the mature domain, or in all three domains.

Accordingly, the genetic alteration can occur at any nucleotide position(s) in the nucleotide sequence of BDNF. For example, the genetic alteration can occur at the beginning, middle or end of the nucleotide sequence. For instance, the genetic alteration can occur anywhere between nucleotides at positions 1 to 1028 of the BDNF nucleotide sequence. Preferably, the genetic alteration occurs in the pre-pro-domain of BDNF, i.e. nucleotides at positions 1-384 of FIG. 1.

Nucleotide additions and deletions refer to the addition and deletion, respectively, of one or more nucleotides in the nucleotide sequence of wild-type BDNF. If more than one nucleotide is added or deleted, the additions and deletions can be contiguous or non-contiguous. Any nucleotide (A, T, C, G), and any combination thereof, can be added or deleted. Additions and deletions may result in a frame shift, or may not result in a frame shift.

A nucleotide substitution refers to the replacement of a nucleotide with a different nucleotide. An example of a substitution is a single nucleotide polymorphism.

A single nucleotide addition, deletion, or substitution within the genome of a person is a genetic alteration, which is herein referred to as a single nucleotide polymorphism (SNP). More specifically, a SNP may be a single base insertion or deletion variant. A SNP substitution can be considered a transition or a transversion. A transition is the replacement of one purine nucleotide by another purine nucleotide, or one pyrimidine by another pyrimidine. A transversion is the replacement of a purine by a pyrimidine, or vice versa.

The standard nomenclature for representing a SNP by those skilled in the art is by a reference SNP number (rs#).

In one embodiment, the genetic alteration is a SNP in which the G nucleotide at position 196 of wild-type BDNF as shown in FIG. 1 is substituted with the nucleotide A. Such SNP is referred to as "G196A." The reference SNP number for G196A is rs6265.

In another embodiment, the genetic alteration is an SNP in which the C nucleotide at position 5 of wild-type BDNF is substituted with the nucleotide T. Such SNP is referred to as "C5T" (rs#8192466).

In yet another embodiment, the genetic alteration is an SNP in which the G nucleotide at position 225 of wild-type BDNF is substituted with the nucleotide T. Such SNP is referred to as "G225T" (rs#1048218).

In another embodiment, the genetic alteration is an SNP is which the G nucleotide at position 374 of wild-type BDNF is substituted with the nucleotide T. Such SNP is referred to as "G374T" (rs#1048220).

In a further embodiment, the genetic alteration is an SNP in which the G nucleotide at position 380 of wild-type BDNF is substituted with the nucleotide T. Such SNP is referred to as G380T (rs#1048221).

In yet a further embodiment, the genetic alteration can be a combination of any of the SNPs described above.

A genetic alteration may occur within one copy or both copies of a BDNF allele. A patient's homologous chromosomes may comprise identical alleles of the BDNF gene at corresponding loci, in which case, the patient's BDNF genotype is homozygous for the BDNF gene. Alternatively, a patient's homologous chromosomes may not comprise identical alleles of the BDNF gene at corresponding loci, in which case, the person's BDNF genotype is heterozygous for the BDNF gene.

The patient's BDNF genotype can be homozygous or heterozygous for any genetic alteration, such as those mentioned above. For example, a patient may be homozygous or heterozygous for any SNP. In one embodiment, the BDNF genotype is homozygous for G196A. In another embodiment, the BDNF genotype is heterozygous for G196A.

The determination of an allele having a genetic alteration can be made by any method known to those skilled in the art. Suitable methods are provided in the "General Methods" section below.

In another embodiment, the determination of a genetic alteration comprises observing expression of a BDNF protein containing an amino acid alteration. The amino acid sequence of wild-type BDNF protein is shown in FIG. 2. The amino acid sequence of the wild-type BDNF pre-domain (signal peptide) comprises the sequence beginning at amino acid residue 1 and ending at residue 18 of FIG. 2. The amino acid sequence of wild-type BDNF pro-domain comprises the sequence beginning at amino acid residue 19 and ending at residue 128 of FIG. 2. The amino acid sequence of wild-type BDNF mature domain comprises the sequence beginning at amino acid residue 129 and ending at residue 247 of FIG. 2.

Typically, the pre-pro-domain of the BDNF protein is cleaved from the mature domain. BDNF protein includes the complete (i.e., uncleaved) protein, cleaved protein, and precursor protein. In wild-type BDNF protein, the complete protein is amino acid residues 1 to 247 of FIG. 2, the cleaved protein is amino acid residues 128 to 247 of FIG. 2, and the precursor protein is amino acid residues 1 to 127 of FIG. 2.

In one embodiment, the method comprises observing whether the patient expresses an uncleaved BDNF protein. In another embodiment, the method comprises observing whether the patient expresses a cleaved BDNF protein. In another embodiment, the method comprises observing whether the patient expresses a precursor BDNF protein.

The term "amino acid alteration" refers to any changes in the amino acid sequence of wild-type BDNF protein. Thus, BDNF proteins that contain an amino acid alteration will have a different amino acid sequence than wild-type BDNF protein. Examples of amino acid alterations include one or more amino acid additions, deletions, substitutions, etc. and combinations thereof, e.g. any of the amino acid alterations caused by the genetic alterations described above.

A nucleic acid substitution that changes a codon coding for one amino acid to a codon coding for a different amino acid is referred to as a non-synonymous codon change, or missense mutation. One type of non-synonymous codon change is a nonsense mutation, which results in the formation of a stop codon, thereby leading to premature termination of a polypeptide chain and a defective protein.

In one embodiment, the amino acid alteration is a substitution of the amino acid valine at position 66 of wild-type BDNF, shown in FIG. 2, with methionine. The nomenclature for representing such an alteration is known by those skilled in the art as val66met.

In another embodiment, the amino acid alteration is a substitution of the amino acid threonine at position 2 of wild-type BDNF with isoleucine. The nomenclature for representing such an alteration is known by those skilled in the art as thr2ile.

In yet another embodiment, the amino acid alteration is a substitution of the amino acid glutamine at position 75 of wild-type BDNF with the amino acid histidine. The nomenclature for representing such an alteration is known by those skilled in the art as gln75his.

In a further embodiment, the amino acid alteration is a substitution of the amino acid arginine at position 125 of wild-type BDNF with the amino acid methionine. The nomenclature for representing such an alteration is known by those skilled in the art as arg125met.

In yet a further embodiment, the amino acid alteration is a substitution of the amino acid arginine at position 127 of wild-type BDNF with the amino acid leucine The nomenclature for representing such an alteration is known by those skilled in the art as arg127leu.

The observation of expression of a BDNF protein having an amino acid alteration can be made by any method known to those skilled in the art. Suitable methods are provided in the "General Methods" section below.

Correlating the Presence of a Genetic Alteration with Susceptibility or Resistance The term "correlate" or "correlating" refers to relating the presence of a BDNF allele having a genetic alteration with susceptibility or resistance to treatment with a compound that activates the brain serotonin system. The determination whether a BDNF allele has a genetic alteration can be carried out without the need for a qualified medical practitioner. For example, a technician in a laboratory that specializes in identifying genetic alterations can perform the correlation step, and inform the medical practitioner of the results.

In a pre-adult patient, the presence of a BDNF allele having a genetic alteration is correlated with susceptibility to treatment with a compound that activates the brain serotonin system.

A patient who is susceptible to treatment with a compound that activates the brain serotonin system refers to a patient who will receive a clinically beneficial effect in response to treatment with the compound. Preferably, such a patient obtains an effect in their condition that is at least as clinically beneficial an effect as does a patient who is of approximately the same age, is homozygous for wild-type BDNF, and is treated with a compound that activates the brain serotonin system for the same condition.

An effect that is clinically beneficial refers to an effect that yields some degree of benefit to at least some part of a patient population following treatment with a compound that activates the brain serotonin system. For example, an effect that is clinically beneficial includes prolongation of the life span of the patient having the condition, inhibition of the progression of the condition, reduction in the rate of disease progression in the patient, remission or regression of the disease in the patient, or improvement in the quality of life of a patient having the condition.

In an adult patient, the presence of a BDNF allele having a genetic alteration is correlated with resistance to treatment with a compound that activates the brain serotonin system. A patient who is resistant to treatment with a compound that activates the brain serotonin system will not receive a significant clinically beneficial effect in response to treatment with the compound.

Adult patients who are homozygous for a genetic alteration generally have little or no significant beneficial effect from compounds that activate the brain serotonin system. For example, compounds that activate the brain serotonin system do not significantly alleviate the patient's condition.

Adult patients who are heterozygous for a genetic alteration generally have a decreased effect from the compounds as compared to patients who are homozygous for the wild-type BDNF genotype. For example, the effect may be decreased by at least about 25%, 50% or 75% with respect to patients who are wild-type homozygous.

Any method known to those of ordinary skill in the art can be used to determine whether a compound that activates the brain serotonin system has a clinically beneficial effect on a patient's condition. For example, a rating scale can be utilized to score the severity of a psychiatric disorder. The patient is then monitored to determine the chronological effect of such a compound. Examples of such rating scales include the Hamilton Rating Scale for Depression (HAM-D), Emotional State Questionnaire or Global Clinical Impression Scale.

The information that a patient is susceptible or resistant to a compound that activates the brain serotonin system is very useful. For example, medical personnel may be able to determine whether to prescribe treatments other than the administration of such compounds for patients who are resistant to the compound. Examples of such other treatments include vagus nerve stimulation, electroconvulsive therapy, transcranial magnetic stimulation, lithium, gamma-amino butyric acid agonists (e.g., pregabalin (Lyrica™)), and dopamine specific agonists (e.g., buproprion (Wellbutrin™)).

Compound

Patients are tested for susceptibility or resistance to any compound that activates the brain serotonin system. Serotonin is a neurotransmitter generally secreted by nerve cells. Typically, some of the secreted serotonin is reabsorbed by the cell that secreted it. Such reabsorption is called serotonin reuptake.

Activation of the brain serotonin system by the compound increases the level of serotonin in the brain. The compound can activate the brain serotonin system by any mechanism known to those in the art. For example, the compound can increase secretion levels by increasing the secretion of serotonin or by inhibiting the reuptake of serotonin or by upregulating BDNF levels as a mechanism of action. The invention is not limited to any particular mechanism.

Examples of compounds that activate the brain serotonin system include tricyclic antidepressants, selective serotonin reuptake inhibitors (SSRI), selective norepinephrine reuptake inhibitors (SNRI), and serotonin antagonist and reuptake inhibitors (SARI).

Examples of tricyclic antidepressants include amitriptyline hydrochloride (or Amitryptyline) (Elavil™), clomipramine (Anafranil™), desipramine (Norpramin™), doxepin (Sinequan™), imipramine (Tofranil™), nortriptyline (Pamelor™), and protriptyline (Vivactil™). Further commercial examples include Tryptanol, Endep, Elatrol, Tryptizol, Trepiline, and Laroxyl. (See Deuschle, M et al. (2008) Serum Concentrations of Nerve Growth Factor and Brain-Derived Neurotrophic Factor in Depressed Patients before and after Antidepressant Treatment. *Pharmacopsychiatry* 41: 66-71.)

Examples of SSRI include fluoxetine (Prozac™), fluvoxamine (Luvox™), paroxetine (Paxil™), sertaline (Zoloft™), citalopram (Celexa™), and escitalopram oxalate (Lexapro™).

Examples of SNRI include duloxetine (Cymbalta™) and venlafaxine (Effexor™).

Examples of SARI include mirtazapine (Remeron™), nefazodone (Serzone™), and desyrel (Trazodone™).

Examples of compounds that upregulate BDNF levels include AMPA receptor agonists, which are also known as ampakines (See Skolnick, P et al. (2001) Current Perspectives on the Development of Non-Biogenic Amine-Based Antidepressants. *Pharmacological Research* 43(5): 411-22. See also Gall, C M et al. (2003) Chronic Elevation of Brain-Derived Neurotrophic Factor by Ampakines. *JPET* 307:297-305.)

Patient

The patient is a human suffering from a condition (e.g., disease, disorder, etc.) that is susceptible to treatment with a compound that activates the brain serotonin system. The patient is generally diagnosed with the condition by a skilled artisan, such as a medical practitioner (e.g., a psychiatrist), as described above.

The methods of the invention described herein can be employed for patients of any gender, age, ethnic population, or genotype. Accordingly, the term "patient" includes males and females, and it includes pre-adults, transition age patients, and adults, as described above.

Examples of ethnic populations include Caucasians, Asians, Hispanics, Africans, African Americans, Native Americans, Semites, and Pacific Islanders. The methods of the invention may be more appropriate for some ethnic populations such as Caucasians, especially northern European populations, as well as Asian populations.

The term "patient" also includes patients of any genotype or phenotype. For example, the patient can have a genotype that is homozygous for the wild-type BDNF gene or homozygous for any BDNF genetic or amino acid alteration or heterozygous for any BDNF genetic or amino acid alteration, such as those mentioned above. In addition, the patient can have the genotype or phenotype for any hair color, eye color, skin color or any combination thereof.

The term "patient" includes a patient of any body height, body weight, or any organ or body part size or shape. For example, the patient can have, for example, an altered anatomy of the hippocampus, amygdala, or prefrontal cortex, in comparison to a patient whose genotype is homozygous for the wild-type BDNF allele.

Condition

The conditions that are susceptible to treatment with a compound that activates the brain serotonin system include any medical disorder. The medical disorder may be a psychiatric disorder or a disease resulting from a genetic or amino acid alteration of BDNF.

Examples of psychiatric disorders include affective disorders, which are characterized by dramatic changes or extremes of mood. Affective disorders can include depression (e.g., major depression, minor depressive disorder), bipolar disorder, dysthymia, anxiety disorder (e.g., generalized anxiety disorder, chronic anxiety disorder, panic disorder, obsessive compulsive disorder, post-traumatic stress disorder, agoraphobia, social phobia), and premenstrual dysphoric disorder.

Other psychiatric disorders include cyclothymic disorder, acute stress disorder, personality disorders, attention deficit/hyperactivity disorder (AD/HD), and substance use disorders. Examples of psychiatric disorders also include eating disorders such as bulimia nervosa and anorexia nervosa.

The medical disorder may also include chronic pain. Examples of chronic pain include diabetic neuropathy and postherpetic neuralgia.

Promoting Normal Brain Development

The inventors have surprisingly discovered that upregulating BDNF levels during a period of growth and development in patients who have a genetic alteration in a BDNF allele impacts the patient's brain in adulthood. Upon reaching adulthood, such patients have brains that developed more similarly to patients who are wild-type for the BDNF gene. Therefore, another aspect of the invention relates to a method for promoting normal brain development in pre-adult patients or transition age patients whose genome contains at least one copy of a BDNF allele having a genetic alteration. The method includes prescribing an effective amount of a compound that upregulates BDNF levels until the patient is an adult.

Promoting normal brain development refers to maintaining, inducing, stimulating, improving, or accelerating development of the patient's brain such that the development is comparable to that observed in patients who are normal or wild-type for the BDNF allele. A wild-type gene is that which is most frequently observed in a population and is designated the "normal" or "wild-type" form of the gene.

A compound that upregulates BDNF levels refers to a compound that causes an increase of expression of the BDNF gene or of the polypeptide encoded by the BDNF gene. For example, the compound may increase expression of mRNA levels of a nucleic acid encoding BDNF or increase expression of BDNF polypeptide levels. Examples of such compounds may include the compounds listed above as a compound that activates the brain serotonin system.

Prescribing the compound "until the patient is an adult" refers to prescribing the compound until the patient has reached a stage in development of being an adult, as described above. For example, the prescribing can continue until the patient has reached full growth and development or has reached the age of approximately 23 years old.

Evidence for Invention

The invention described herein was confirmed by experiments in mice. Mouse ages can be corresponded with human ages, roughly as follows: Prepubertal age in humans (approximately ages 5-8 years old) can correspond to approximately postnatal day 23-33 (P23-P33) in mice. An early pubertal age in humans (approximately ages 9-10 years old) can correspond to approximately postnatal day 33-36 in mice. A midpubertal age in humans (approximately ages 11-17 years old) can correspond to approximately postnatal day 36-45 in mice. A late pubertal age in humans (approximately ages 18-22) can correspond to approximately postnatal day 46-49 in mice. A post-pubertal age in humans (approximately ages 23-55 years old) can correspond to approximately postnatal day 49-61 in mice. An elderly age in humans (approximately ages 70 years old or older) can correspond to approximately postnatal day 300 and on. See, for example, Adriani et al. (2004). *Neurospychopharmacology*, 29(5): 869-878, and Dohler, K. et al. (1975) *Endocrinology*, 97(4): 898-907.

The experiments included studies using behavioral paradigms that are known in the art for studying conditions that are susceptible to treatment with a compound that activates the brain serotonin system. The behavioral paradigms include open field, elevated plus maze, and novelty induced hypophagia (NIH).

The open field and elevated plus maze tests are well validated studies for conditions that are susceptible to treatment with a compound that activates the brain serotonin system. They have shown to have predictive value for drug efficacy, initially with GABAergic drugs (see Crawley, *Neurosci. Biobehav. Rev.* 1985 Spring 9(1):37-44). The open field test has been validated a reliable test for modeling the anti-anxiety effects of chronic fluoxetine (Dulawa et al., *Neuropsychopharmacology.* 2004 Jul. 29(7):1321-30). In addition, this effect of chronic fluoxetine using the open field test was replicated in Chen et al., *Science,* 6 Oct. 2006:314(5796): 140-143. The effect was also replicated in the elevated plus maze (unpublished data).

The novelty induced hypophagia (NIH) test is also a well validated study for conditions that are susceptible to treatment with a compound that activates the brain serotonin system (Dulawa et al. *Neurosci Biobehav Rev.* 2005 29(4-5):771-83). For example, the NIH model is a powerful model with predictive and construct validity for anxiolytic effects of chronic antidepressant treatment. Predictive validity is defined as the ability of a model to make accurate predictions about the human phenomenon of interest.

In order to increase the feasibility of carrying out the large number of behavioral tasks proposed, all of the behavior tests can be automated with the aid of video tracking software (EthoVision 3.0, Noldus Observer), and validated through comparison with standard scoring of behaviors from video recordings.

General Methods

To observe whether the genome of a patient contains at least one copy of the BDNF allele containing a genetic alteration, a sample containing the patient's DNA is obtained. Examples of such samples include blood, salvia, urine and epithelial cells.

The sample can be obtained by any method known to those in the art. Suitable methods include, for example, venous puncture of a vein to obtain a blood sample and cheek cell scraping to obtain a buccal sample.

DNA can be isolated from the sample by any method known to those in the art. For example, commercial kits, such as the QIAGEN System (QIAmp DNA Blood Midi Kit, Hilder, Germany) can be used to isolate DNA.

The DNA is optionally amplified by methods known in the art. One suitable method is the polymerase chain reaction (PCR) method described by Saiki et al., *Science* 239:487 (1988), U.S. Pat. No. 4,683,195 and Sambrook et al. (Eds.), Molecular Cloning, Third Edition, Cold Spring Harbor Laboratory Press, Cold Spring Harbor, N.Y. (2001). For example, oligonucleotide primers complementary to a nucleotide sequence flanking and/or present at the site of the genetic alteration of the allele can be used to amplify the allele.

The isolated DNA is used to determine whether an allele containing a genetic alteration is present in the sample. The presence of an allele containing a genetic alteration can be determined by any method known to those skilled in the art. One method is to sequence the isolated DNA and compare the sequence to that of wild-type BDNF.

Alternative methods include, for example, use of nucleic acid probes and polymerase chain reaction (PCR). Methods for making and using nucleic acid probes are well documented in the art. For example, see Keller G H and Manak M M, *DNA Probes,* 2$^{nd}$ ed., Macmillan Publishers Ltd., England (1991) and Hames B D and Higgins S J, eds., *Gene Probes I* and *Gene Probes II*, IRL Press, Oxford (1995).

For example, methods for distinguishing a wild-type allele from an allele containing a single nucleotide change are described in PCT Application WO 87/07646. The methods disclosed in PCT Application WO 87/07646 are incorporated herein by reference.

Briefly, oligonucleotides containing either the wild-type or an allele containing a genetic alteration are hybridized under stringent conditions to dried agarose gels containing target RNA or DNA digested with an appropriate restriction endonuclease. An example of suitable stringent conditions includes a temperature of two or more degrees below the calculated $T_m$ of a perfect duplex. The oligonucleotide probe hybridizes to the target DNA or RNA detectably better when the probe and the target are perfectly complementary.

A particularly convenient method for assaying a single point mutation by means of oligonucleotides is described in Segev, PCT Application WO 90/01069. The methods disclosed in PCT Application WO 90/01069 are hereby incorporated by reference.

Briefly, two oligonucleotide probes for a wild-type and an allele containing a genetic alteration being assayed are prepared. Each oligonucleotide probe is complementary to a sequence that straddles the nucleotides at the site of the genetic alteration. Thus, a gap is created between the two hybridized probes.

The gap is filled with a mixture of a polymerase, a ligase, and the nucleotide complementary to that at the position to form a ligated oligonucleotide product. Either of the oligonucleotides or the nucleotide filling the gap may be labelled by methods known in the art.

The ligated oligonucleotide product can be amplified by denaturing it from the target, hybridizing it to additional oligonucleotide complement pairs, and filling the gap again, this time with the complement of the nucleotide that filled the gap in the first step.

The oligonucleotide product can be separated by size and the label is detected by methods known in the art.

Alleles containing a genetic alteration may also be detected if they create or abolish restriction sites; see Baker et al., Science 244, 217-221 (1989). Some additional examples of the use of restriction analysis to assay point mutations are given in Weinberg et al., U.S. Pat. No. 4,786,718 and Sands, M. S. and Birkenmeier, E. H., Proc. Natl. Acad. Sci. USA 90:6567-6571 (1993).

For example, point mutations can be detected by means of single-strand conformation analysis of polymerase chain reaction products (PCR-SSCP). This method is described in Orita, M. et al., Proc. Natl. Acad. Sci. USA 86:2766-2770 (1989), Suzuki, Y. et al., Oncogene 5:1037-1043 (1990), and Sarkar, F. H. et al., Diagn. Mol. Pathol. 4:266-273 (1995).

Some additional methods for distinguishing a wild-type allele and allele containing a genetic alteration are described by De Ley et al., J. Bacteriol. 101:738-754 (1970); Wood et al., Proc. Natl. Acad. USA 82:1585-1588 (1985); Myers et al., Nature 313:495-497 (1985); and Myers et al., Science 230: 1242-1246 (1985).]. See also U.S. Patent Application Publication No. 2005/0014170, which discloses assays for observing BDNF genotypes, the specification of which is hereby incorporated by reference.

To observe whether the patient expresses a BDNF protein containing an amino acid alteration, a sample containing protein is obtained. The sample can be any sample which contains protein. Examples of such samples include blood and spinal fluid. The sample can be obtained by any method known to those in the art.

Protein can be isolated from the sample by any method known to those in the art. For example, commercial kits, such as the Mono Q ion exchange chromatography (Amersham Biosciences, Piscataway, N.J.) can be used to isolate the protein.

The protein can be used, for example, to generate antibodies. The antibody may be polyclonal or monoclonal. Polyclonal antibodies can be isolated from mammals that have been inoculated with the protein in accordance with methods known in the art.

Briefly, polyclonal antibodies may be produced by injecting a host mammal, such as a rabbit, mouse, rat, or goat, with the protein or fragment thereof capable of producing antibodies that distinguish between proteins containing amino acid alterations and wild-type protein. The peptide or peptide fragment injected may contain the wild-type sequence or the sequence containing the amino acid alteration. Sera from the mammal are extracted and screened to obtain polyclonal antibodies that are specific to the peptide or peptide fragment.

The antibodies are preferably monoclonal. Monoclonal antibodies may be produced by methods known in the art. These methods include the immunological method described by Kohler and Milstein in Nature 256, 495-497 (1975) and by Campbell in "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985), as well as the recombinant DNA method described by Huse et al. in Science 246, 1275-1281 (1989).

In order to produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein in Nature 256, 495-497 (1975). See also Campbell, "Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1985). In order to be useful, a peptide fragment must contain sufficient amino acid residues to define the epitope of the molecule being detected (e.g., distinguish between wild-type protein and proteins containing amino acid alterations).

The antibodies can, for example, be used to observe the presence of BDNF proteins containing amino acid alterations. Suitable methods include, for example, a Western blot and an ELISA assay.

EXAMPLES

Example 1

Determining the Developmental Onset of Anxiety-Like Behavior in BDNF$^{Met/Met}$ Mice Behavioral and Anatomical Defects in BDNF$^{Met/Met}$ Knock-in Mice.

A gene-targeted BDNF knock-in mouse containing the genetic variant form of BDNF (BDNF$^{Met/Met}$) was generated. The details of the targeting vector used to generate the BDNF$_{Met}$ mouse as well as validation of this mouse model have recently been published (Z. Y. Chen et al., Science 314, 140 (Oct. 6, 2006). Anxiety symptoms have been shown to be a prevalent endophenotype in a variety of affective disorders and one that has been reliably modeled in rodents (S. C. Dulawa, R. Hen, Neurosci Biobehav Rev 29, 771 (2005)).

FIG. 3A depicts how the Met substitution in the prodomain of BDNF in neurosecretory cells and primary cultured neurons lead to three trafficking defects: (1) decreased variant BDNF$_{Met}$ distribution into neuronal dendrites; (2) decreased variant BDNF targeting to secretory granules; and (3) subsequent impairment (of ~30%) in regulated secretion (M. F. Egan, D. R. Weinberger, B. Lu, Am J Psychiatry 160, 1242 (July, 2003); Z. Y. Chen et al., J Neurosci 25, 6156 (Jun. 29, 2005); Z. Y. Chen et al., J Neurosci 24, 4401 (May 5, 2004)). This variant BDNF provides an example of how trafficking of BDNF may have significant impact on the physiological responses to neurotrophins.

The analyses are focused on identifying abnormal components of psychiatric disorders in the BDNF$^{Met/Met}$ mice, as these endophenotypes are likely to have fewer genetic determinants. In this manner, a more precise understanding of the contribution of one SNP can be determined. The initial behavioral analyses of adult BDNF$^{Met/Met}$ mice elucidated a phenotype that had not been established in human carriers: increased anxiety.

Figure 4:
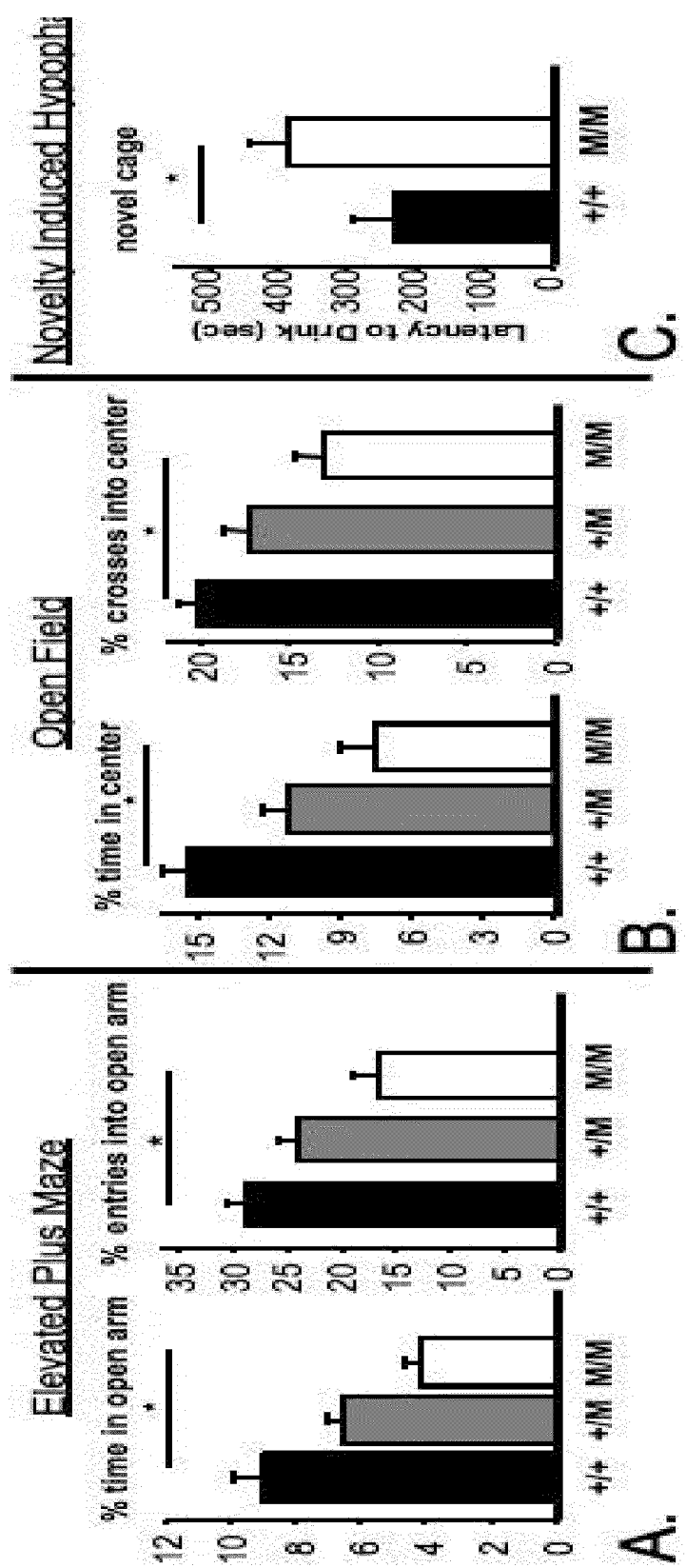
FIG. 4. Anxiety-related behavior in $BDNF^{Met/Met}$ (M/M), $BDNF^{+/Met}$ (+/M), and BDNF wild-type (+/+) mice in the elevated plus maze (A) and open field tests (B).

When placed in stressful settings, BDNF$^{Met/Met}$ mice display increased anxiety-related behaviors in three separate tests (open field, elevated plus maze, novelty induced hypophagia), and thus provide a genetic link between BDNF and anxiety (FIG. 4).

In the preliminary studies, P60 BDNF$^{Met/Met}$ mice were observed to have elevated levels of anxiety-related behaviors. When BDNF$^{Met/Met}$ mice were tested at earlier ages (P30), which corresponds to adolescence in humans, no significant alteration in anxiety-like behavior was observed in the elevated plus maze or open field test (data not shown). Accordingly, the onset of this endophenotype for affective disorders occurs in a timeframe or "critical time" between adolescence and adulthood in BDNF$^{Met/Met}$ mice, and provides a unique developmental window to delineate changes in brain circuitry related to anxiety.

Figure 5:
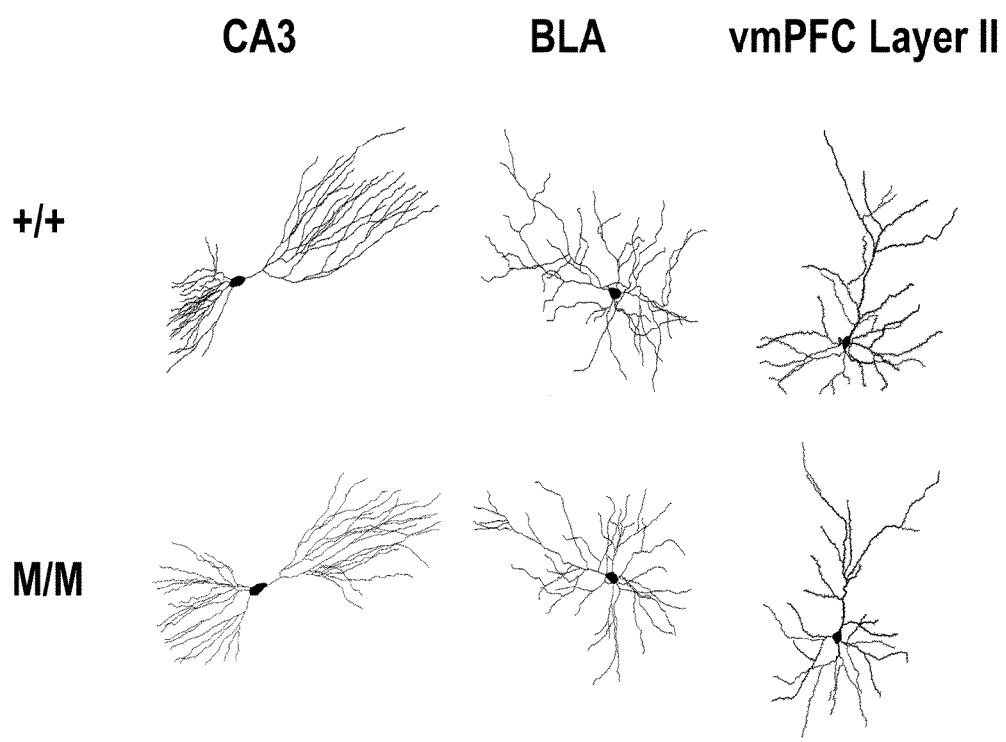
FIG. 5. Effect of variant $BDNF_{Met}$ on hippocampal, amygdala, and prefrontal cortical neuronal morphology during adulthood. Examples of Golgi-stained CA3 hippocampal, basolateral amygdala (BLA), and prefrontal cortical (vmPFC, Layer II) neurons from adult (P60) wild-type (+/+) and homozygous (M/M) mice.

Subsequent anatomical analyses in adult BDNF$^{Met/Met}$ mice found alteration in the volume, as well as altered neuronal morphology regions of the brain implicated in mediating anxiety-related behaviors including the amygdala, prefrontal cortex, and hippocampus (FIG. 5). Accordingly, these regions have abnormal development.

Example 2

Figure 6:
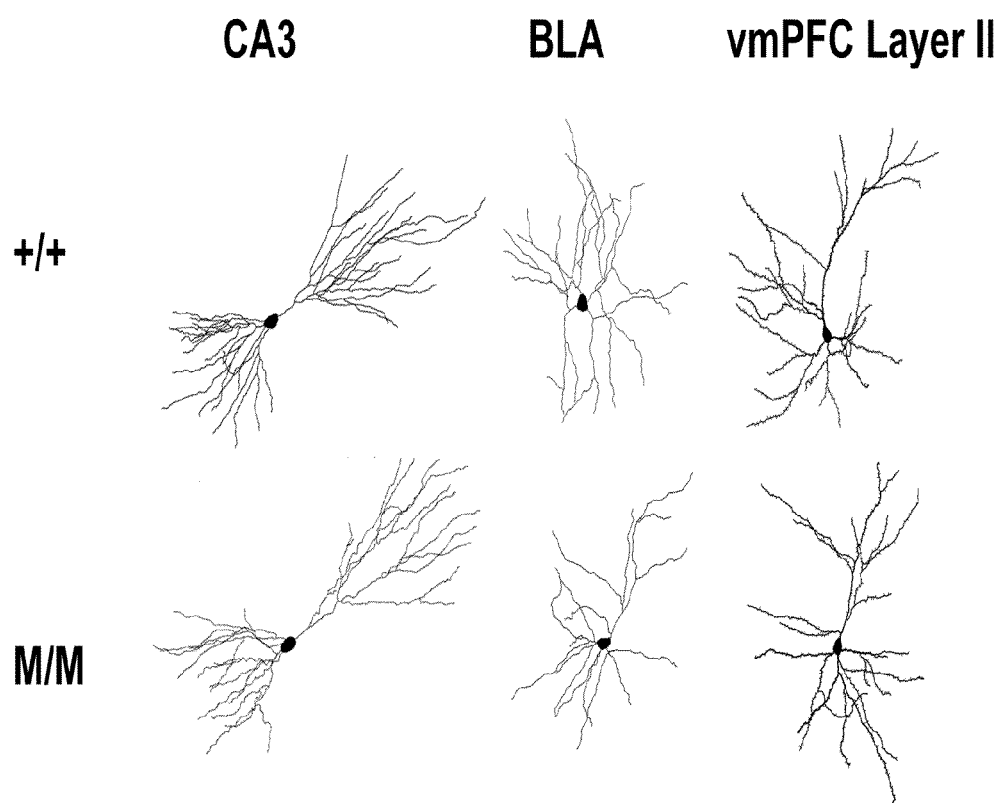
FIG. 6. Effect of variant $BDNF_{Met}$ on hippocampal, amygdala, and prefrontal cortical neuronal morphology during adolescence (P30). Examples of Golgi-stained CA3 hippocampal, basolateral amygdala (BLA), and prefrontal cortical (vmPFC, Layer II) neurons from adult (P30) wild-type (+/+) and homozygous (M/M) mice.

Behavioral, Anatomical, Neuronal Morphology Analyses Across Development in BDNF$_{Met}$ Mice The following were traced: CA3 hippocampal neurons (FIG. 6), BLA pyramidal neurons, and vmPFC pyramidal neurons at P30 and show decreased dendritic complexity in BDNF$^{Met/Met}$ mice across regions at both ages for Hc and BLA neurons as in P60 (FIG. 5), but not for vmPFC neurons at P30 (FIG. 6). Accordingly, alterations in the vmPFC between P30 and P60 may be involved in the emergence of the anxiety phenotype in the BDNF$^{Met/Met}$ mice.

Example 3

A common treatment for depression and anxiety disorders in humans is administering serotonin reuptake inhibitors (SSRI's), for which one postulated mechanism of action involves increasing BDNF levels (R. S. Duman, L. M. Monteggia, Biol Psychiatry 59, 1116 (Jun. 15, 2006)). Adult P60 BDNF$^{Met/Met}$ mice were treated orally with fluoxetine (18 mg/kg of body weight per day) or vehicle for 21 days before assessment in novelty-induced hypophagia. In this conflict test, mice are trained to approach a reward (sweetened milk) in their home cage and then placed in a novel brightly lit cage. The latency to approach and drink the sweetened milk is a measure of the anxiety-related behavior associated with this task (S. C. Dulawa, K. A. Holick, B. Gundersen, R. Hen, *Neuropsychopharmacology* 29, 1321 (July, 2004)).

Figure 7:
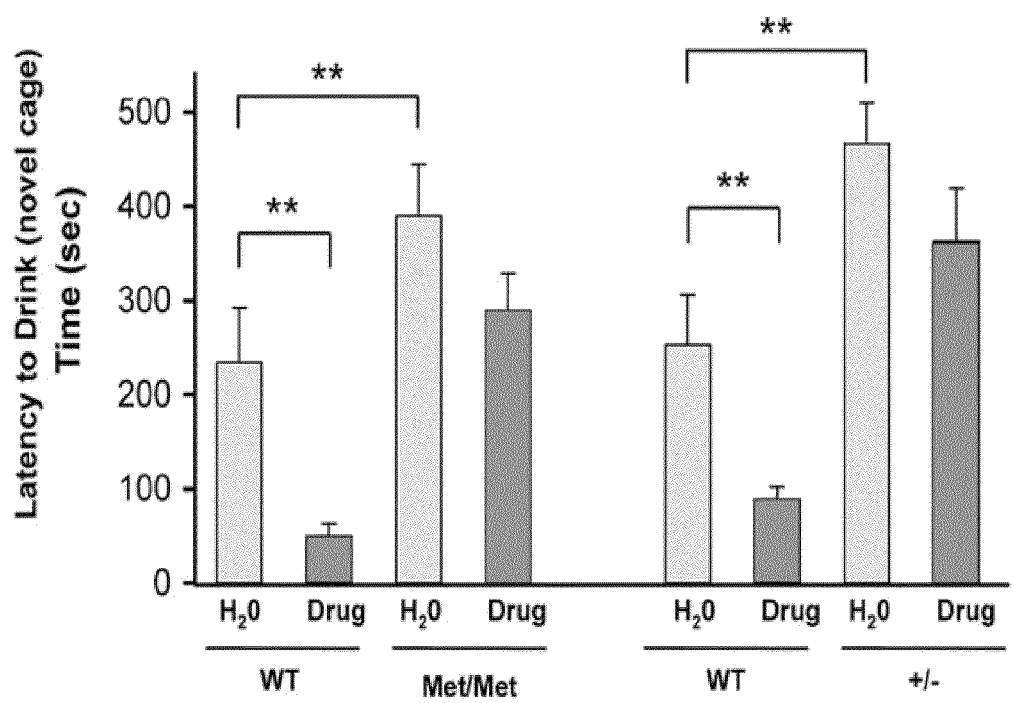
FIG. 7. Graphic representation of time and duration of fluoxetine (FLX) administration, and anticipated effects on CNS BDNF levels.

BDNF$^{Met/Met}$ mice treated with vehicle had a significantly greater latency to drink in the novel cage as compared with WT controls (FIG. 7). Treatment with long-term fluoxetine did not significantly decrease the latency to drink in BDNF$^{Met/Met}$ mice, as in WT littermate mice treated in parallel with long-term fluoxetine (FIG. 7). Thus, the form of anxiety elicited in these BDNF$^{Met/Met}$ mice was not responsive to a common SSRI, which is consistent with a previous BDNF knock-out mice studies in which decreased BDNF levels led to decreased antidepressant response (R. S. Duman, L. M. Monteggia, *Biol Psychiatry* 59, 1116 (Jun. 15, 2006); L. M. Monteggia et al., *Biol Psychiatry* 61, 187 (Jan. 15, 2007)).

Of note, these adult BDNF$^{Met/Met}$ mice have been established to exhibit increased anxiety-like behavior (FIG. 4). Accordingly, they were of an age past the "critical time" for emergence of the increased anxiety endophenotype and this SNP contributes to this high non-response rate.

Example 4

Effect of BDNF Genotype on Timed Antidepressant Response in BDNF$_{Met}$ Mice

It was demonstrated that P60 BDNF$^{Met/Met}$ mice have decreased response to chronic fluoxetine as measured by two anxiety tests (FIG. 7). It was chosen to continue to use fluoxetine as it is the prototypic SSRI that has been established to increase BDNF levels, and for which a significant amount of clinical data on response to affective disorders.

Example 5

In this example, the following was investigated: whether timing of SSRI administration, which raises CNS BDNF levels during the "sensitive period," rescues this altered anxiety phenotype in adulthood.

Figure 8:
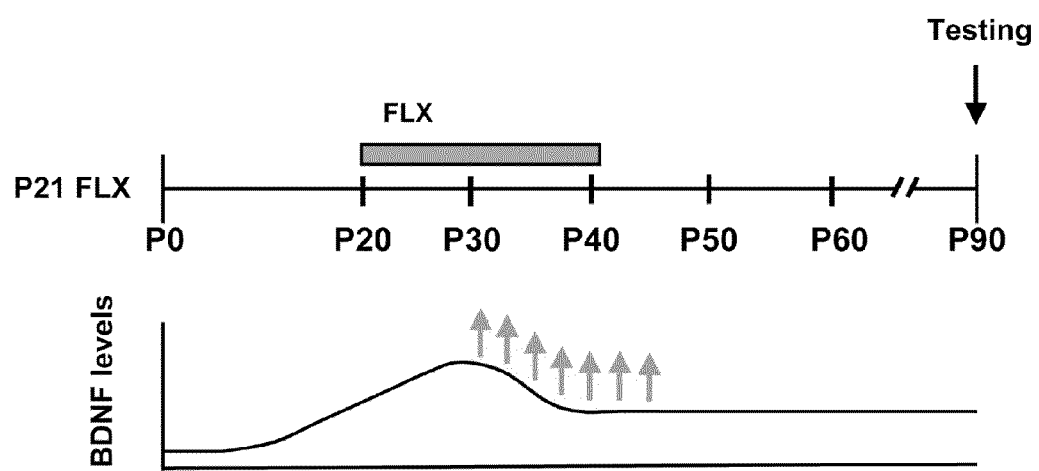
FIG. 8. Graphic representation of time and duration of fluoxetine (FLX) administration, and anticipated effects on CNS and BDNF levels.

The feasibility of these timed pharmacological studies was first assessed. To BDNF$_{Met}$ mice, chronic fluoxetine (18 mg/kg per day) was administered via the drinking water from P21 (post-weaning)-P40 (adolescence) (FIG. 8) for a duration of time established to produce increased BDNF levels and anti-anxiety effects in adult mice [Dulawa, S. C., Holick, K. A., Gundersen, B., and Hen, R. (2004). Effects of chronic fluoxetine in animal models of anxiety and depression. Neuropsychopharmacology 29, 1321-1330; Duman, R. S., and Monteggia, L. M. (2006). A neurotrophic model for stress-related mood disorders. Biol Psychiatry 59, 1116-1127].

Figure 9:
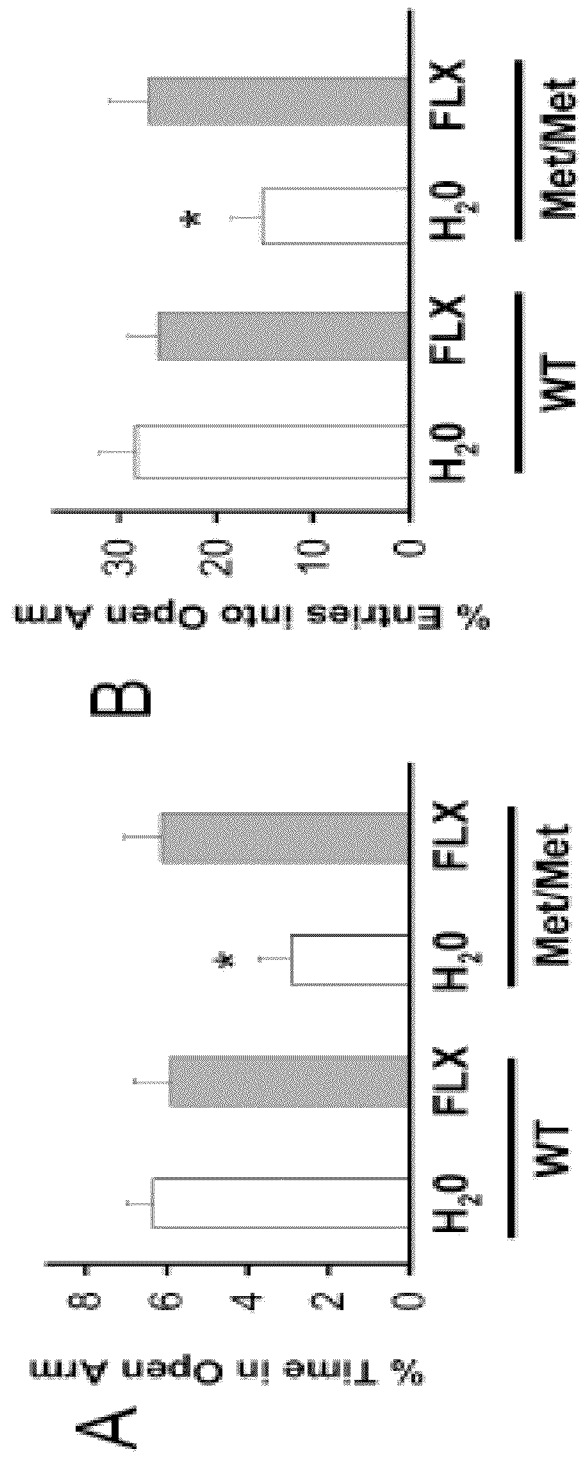
FIG. 9. Anxiety-related behavior after early life flouxetine in BDNF Val66Met mice in the elevated plus maze test. (A).
Figure 9:
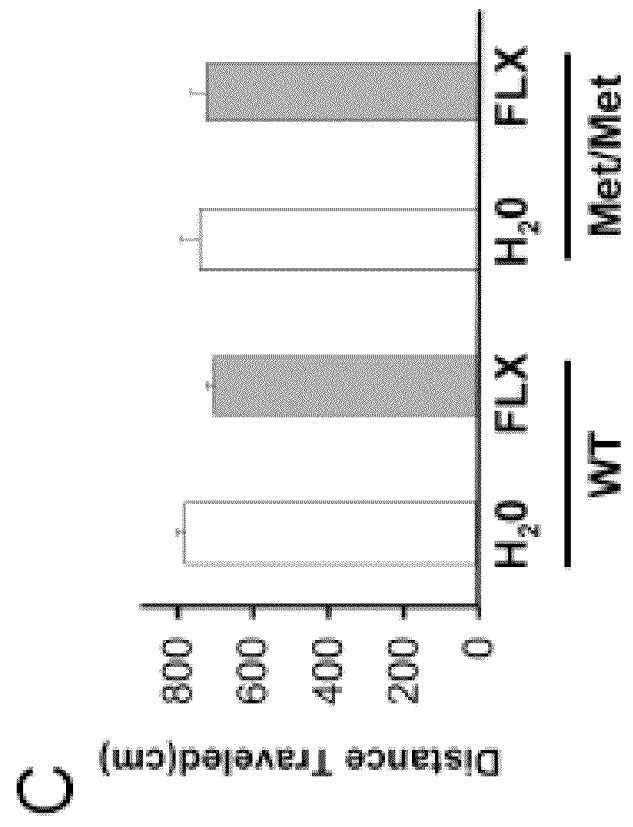

At P90 (adulthood), a time point significantly beyond the last fluoxetine dosing, baseline anxiety-related behavior in the elevated plus maze test in mice treated with or without early life fluoxetine was measured. A rescue of altered anxiety-related behavior in the BDNF$^{Met}$ mice in adulthood by this timed early life fluoxetine administration was observed (FIG. 9A, 9B). No effects were observed on anxiety-related behaviors (FIG. 9A, 9B) in wildtype mice by this early life fluoxetine, or on baseline locomotor activity (FIG. 9C). In this context, prior studies have established that earlier timed fluoxetine treatments at P4-P21, can lead to increased anxiety-related behaviors [Ansorge, M. S., Zhou, M., Lira, A., Hen, R., and Gingrich, J. A. (2004). Early-life blockade of the 5-HT transporter alters emotional behavior in adult mice. Science 306, 879-881], which was not observed by this P21-P40 timed treatment.

Accordingly, the serotonin system in this age frame (P21-P40) is functioning to a degree to allow for a reversal of the anxiety behavior phenotype in the BDNF$^{Met/Met}$ mice.

With regard to clinical significance, these studies provide the first evidence that a behavioral alteration observed in the adult BDNF Val66Met mice can be reversed by an early life intervention. In this context, the timed intervention used is a common pharmacological agent for the treatment of affective disorders in humans.

What is claimed is:

1. A method for promoting normal brain development in a pre-adult patient or a transition age patient whose genome contains at least one copy of a BDNF allele having a genetic alteration, wherein the genetic alteration comprises a single nucleotide polymorphism selected from the group consisting of G196A, CST, G225T, G374T and G380T, the method comprising prescribing an effective amount of a compound that upregulates BDNF levels to the pre-adult patient or transition age patient.

2. The method of claim 1, wherein the single nucleotide polymorphism is G196A.

3. The method of claim 1, wherein the single nucleotide polymorphism is CST.

4. The method of claim 1, wherein the single nucleotide polymorphism is G225T.

5. The method of claim 1, wherein the single nucleotide polymorphism is G374T.

6. The method of claim 1, wherein the single nucleotide polymorphism is G380T.

7. The method of claim 1, wherein the patient is homozygous for the BDNF allele.

8. The method of claim 7, wherein the patient is homozygous for G196A.

9. The method of claim 1, wherein the patient is heterozygous for the BDNF allele.

10. The method of claim 1, wherein the patient is heterozygous for G196A.

11. The method of claim 1, wherein the compound is a tricyclic antidepressant, an SSRI, an SNRI, or an SARI.

12. The method of claim 1, wherein the patient is a pre-adult, and the method further comprises prescribing to the pre-adult patient an effective amount of the compound that activates the brain serotonin system.

13. The method of claim 12, wherein the method further comprises prescribing to the pre-adult patient an effective amount of the compound until the patient is an adult.

14. The method of claim 1, further comprising prescribing to the adult patient a treatment other than administration of the compound.

15. A method for promoting normal brain development in a pre-adult patient or a transition age patient whose genome contains at least one copy of a BDNF allele having a genetic alteration, the method comprising prescribing an effective amount of a compound that upregulates BDNF levels to the pre-adult patient or transition age patient, wherein the compound is a tricyclic antidepressant, an SSRI, an SNRI, or an SARI.

16. The method of claim 15, wherein the genetic alteration comprises a frame shift, one or more nucleotide additions, one or more nucleotide deletions, one or more substitutions, or a single nucleotide polymorphism.

17. The method of claim 15, wherein the single nucleotide polymorphism is selected from the group consisting of G196A, C5T, G225T, G374T and G380T.

18. The method of claim 15, wherein the method further comprises prescribing to the pre-adult patient an effective amount of the compound until the patient is an adult.

19. The method of claim 15, wherein the compound is an SSRI.

* * * * *

UNITED STATES PATENT AND TRADEMARK OFFICE
CERTIFICATE OF CORRECTION

PATENT NO. : 8,853,279 B2
APPLICATION NO. : 12/999581
DATED : October 7, 2014
INVENTOR(S) : Lee et al.

Page 1 of 1

It is certified that error appears in the above-identified patent and that said Letters Patent is hereby corrected as shown below:

IN THE CLAIMS:

Claim 1, column 17, line 62:

Now reads: "CST"

Should read: -- C5T --

Claim 3, column 18, line 57:

Now reads: "CST"

Should read: -- C5T --

Signed and Sealed this
Twenty-second Day of September, 2015

Michelle K. Lee
*Director of the United States Patent and Trademark Office*

SEQUENCE LISTING

<160> NUMBER OF SEQ ID NOS: 2

<210> SEQ ID NO 1
<211> LENGTH: 744
<212> TYPE: DNA
<213> ORGANISM: Homo sapiens

<400> SEQUENCE: 1

```
atgaccatcc ttttccttac tatggttatt tcatactttg gttgcatgaa ggctgccccc      60
atgaaagaag caaacatccg aggacaaggt ggcttggcct acccaggtgt gcggacccat     120
gggactctgg agagcgtgaa tgggcccaag gcaggttcaa gaggcttgac atcattggct     180
gacactttcg aacacgtgat agaagagctg ttggatgagg accagaaagt tcggcccaat     240
gaagaaaaca ataaggacgc agacttgtac acgtccaggg tgatgctcag tagtcaagtg     300
cctttggagc ctcctcttct ctttctgctg gaggaataca aaaattacct agatgctgca     360
aacatgtcca tgagggtccg cgccactct gaccctgccc gccgagggga gctgagcgtg     420
tgtgacagta ttagtgagtg ggtaacggcg gcagacaaaa agactgcagt ggacatgtcg     480
ggcgggacgg tcacagtcct tgaaaaggtc cctgtatcaa aaggccaact gaagcaatac     540
```

```
ttctacgaga ccaagtgcaa tcccatgggt tacacaaaag aaggctgcag gggcatagac    600
aaaaggcatt ggaactccca gtgccgaact acccagtcgt acgtgcgggc ccttaccatg    660
gatagcaaaa agagaattgg ctggcgattc ataaggatag acacttcttg tgtatgtaca    720
ttgaccatta aaagggaag atag                                           744

<210> SEQ ID NO 2
<211> LENGTH: 247
<212> TYPE: PRT
<213> ORGANISM: Homo sapiens

<400> SEQUENCE: 2

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245
```